United States Patent
Marsh et al.

(10) Patent No.: US 11,883,513 B2
(45) Date of Patent: Jan. 30, 2024

(54) HAIR STRENGTHENING COMPOSITION

(71) Applicant: The Procter & Gamble Company, Cincinnati, OH (US)

(72) Inventors: Jennifer Mary Marsh, Deerfield Township, OH (US); Timothy James Felts, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 17/114,767

(22) Filed: Dec. 8, 2020

(65) Prior Publication Data

US 2021/0169760 A1    Jun. 10, 2021

Related U.S. Application Data

(60) Provisional application No. 62/945,959, filed on Dec. 10, 2019.

(51) Int. Cl.

| | | |
|---|---|---|
| *A61K 8/362* | (2006.01) | |
| *A61K 8/04* | (2006.01) | |
| *A61K 8/34* | (2006.01) | |
| *A61K 8/36* | (2006.01) | |
| *A61K 8/41* | (2006.01) | |
| *A61K 8/46* | (2006.01) | |
| *A61K 8/49* | (2006.01) | |
| *A61K 8/898* | (2006.01) | |
| *A61Q 5/12* | (2006.01) | |

(52) U.S. Cl.
CPC .............. *A61K 8/362* (2013.01); *A61K 8/042* (2013.01); *A61K 8/342* (2013.01); *A61K 8/345* (2013.01); *A61K 8/361* (2013.01); *A61K 8/416* (2013.01); *A61K 8/463* (2013.01); *A61K 8/49* (2013.01); *A61K 8/898* (2013.01); *A61Q 5/12* (2013.01); *A61K 2800/596* (2013.01)

(58) Field of Classification Search
CPC ........ A61K 8/362; A61K 8/042; A61K 8/342; A61K 8/345; A61K 8/361; A61K 8/416; A61K 8/463; A61K 8/49; A61K 8/898; A61K 2800/596; A61Q 5/12; A61Q 5/002
See application file for complete search history.

(56) References Cited

U.S. PATENT DOCUMENTS

| | | | |
|---|---|---|---|
| 10,117,819 B2 | 11/2018 | Marsh et al. | |
| 2001/0008631 A1 | 7/2001 | Ellis et al. | |
| 2004/0208903 A1* | 10/2004 | Robinson | A61K 8/44 424/70.13 |
| 2010/0004338 A1 | 1/2010 | Sen et al. | |
| 2011/0077301 A1 | 3/2011 | Deminiere et al. | |
| 2016/0175209 A1 | 6/2016 | Walker et al. | |
| 2016/0279162 A1 | 9/2016 | Richard | |
| 2017/0281523 A1 | 10/2017 | Punyani et al. | |
| 2017/0304182 A1 | 10/2017 | Kadir et al. | |
| 2018/0049969 A1 | 2/2018 | Stella et al. | |
| 2018/0280270 A1 | 10/2018 | Rughani et al. | |
| 2019/0343835 A1 | 11/2019 | Jordan, III et al. | |

FOREIGN PATENT DOCUMENTS

| | | | | |
|---|---|---|---|---|
| EP | 1800715 A1 * | 6/2007 | | A61K 8/31 |
| JP | 2015078167 A | 4/2015 | | |
| JP | 2017537945 A | 12/2017 | | |
| KR | 20160128250 A | 11/2016 | | |
| KR | 20180096564 A | 8/2018 | | |
| KR | 20190068362 A | 6/2019 | | |
| WO | WO-2017173050 A1 * | 10/2017 | | A61K 8/19 |

OTHER PUBLICATIONS

EP1800715 Eng Tran. Published: Jun. 2007.*
PCT Search Report and Written Opinion for PCT/US2020/070881 dated Mar. 26, 2021.

* cited by examiner

*Primary Examiner* — David J Blanchard
*Assistant Examiner* — Thurman Wheeler
(74) *Attorney, Agent, or Firm* — John G. Powell; Angela Kathryn Haughey

(57) ABSTRACT

Disclosed is a hair care composition comprising from about 0.04 wt % to about 2 wt % azelaic acid; from about 0.04 wt % to about 1 wt % oleic acid; wherein the ratio of oleic acid to azelaic acid is from about 1:1 to about 1:3.

20 Claims, No Drawings

HAIR STRENGTHENING COMPOSITION

FIELD OF THE INVENTION

The present invention relates to a hair care composition comprising azelaic acid and oleic acid to provide an anti-breakage hair strength benefit.

BACKGROUND OF THE INVENTION

A variety of approaches have been developed to improve health of the hair. A common method of providing a hair health benefit is through the use of conditioning agents such as cationic surfactants and polymers, high melting point fatty compounds, low melting point oils, silicone compounds, and mixtures thereof. Most of these conditioning agents are known to provide various hair health benefits. However, it has been found that hair strength is an important benefit, as it helps the hair reduce breakage. Hair breakage is noticed, often as hair loss, by the consumer during hair brushing or styling. It has been found that two actives can significantly improve fatigue strength, thereby minimizing breakage; azelaic acid and oleic acid. When used in combination they result in a synergistic benefit. It is believed that they work by different mechanisms, azelaic acid partitions into the protein region of hair and oleic acid partitions into the lipid cell membrane complex region.

SUMMARY OF THE INVENTION

Disclosed is a hair care composition comprising from about 0.04 wt % to about 2 wt % azelaic acid; from about 0.04 wt % to about 1 wt % oleic acid; wherein the ratio of oleic acid to azelaic acid is from about 1:1 to about 1:3 Oleic:Azelaic; and an aqueous carrier.

DETAILED DESCRIPTION OF THE INVENTION

While the specification concludes with claims particularly pointing out and distinctly claiming the invention, it is believed that the present invention will be better understood from the following description.

Herein, "comprising" means that other steps and other ingredients which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Herein, "mixtures" is meant to include a simple combination of materials and any compounds that may result from their combination.

The term "molecular weight" or "M.Wt." as used herein refers to the weight average molecular weight unless otherwise stated. The weight average molecular weight may be measured by gel permeation chromatography.

"QS" means sufficient quantity for 100%.

Hair Products

The hair care composition comprises azelaic acid and oleic acid. The hair care composition may further comprise materials selected from a cationic surfactant; a high melting point fatty compound; a silicone; an aqueous carrier and combinations thereof. The hair care composition can be a rinse off or a leave on treatment. The hair care composition can be a hair conditioner. The oleic acid and azelaic acid are added in a ratio of from about 1:1 to about 1:3, alternatively from about 1:2.5 to about 1:3 oleic acid to azelaic acid, alternatively from about 1:2 to about 1:3 oleic acid to azelaic acid, alternatively from about 1:1.5 to about 1:3 oleic acid to azelaic acid. Use of the azelaic acid and oleic acid at these ratios results in a synergistic increase of hair strength. A combined strength benefit may be realized with a combination of the acids. It is believed that the two actives partition into different parts of the hair to provide a strength benefit; Oleic acid into the lipid-rich cell membrane complex and azelaic acid into the protein regions of hair Regular bleach hair is dosed at 1.25 mg acid/g hair with 1:3, 1:1, and 3:1 oleic:azelaic acid. The data in Table 1 shows a benefit from a ratio of about 1:1 and an even more improved alpha value for the acids having a higher level of azelaic acid to oleic acid (at the same total amount of acid/gram of hair). The increased benefit resulting from a higher ratio of azelaic acid to oleic acid is likely a result of partitioning since there are larger amounts of proteinaceous regions in the fiber in relation to lipid regions.

TABLE 1

(1.25 mg total acid/g hair)

| | Alpha Value (Fatigue Cycles) # of cycles where 63% of fibers has broken |
|---|---|
| Oleic Acid Only | 1823 |
| 3:1 Oleic:Azelaic | 2563 |
| 1:1 Oleic:Azelaic | 3040 |
| 1:3 Oleic:Azelaic | 4072 |
| Azelaic Acid Only | 2414 |

The hair care composition comprises from about 0.04 wt % to about 2 wt % azelaic acid, alternatively from about 0.1 wt % to about 1 wt % azelaic acid. Azelaic acid is also known as nonanedioic acid and is a saturated dicarboxylic acid; available from Sigma-Aldrich. It has been used in skin care products for the treatment of mild cases of acne and skin hyperpigmentation.

The hair care composition comprises from about 0.04 wt % to about 2 wt % oleic acid, alternatively from about 0.1 wt % to about 0.5 wt % oleic acid. Oleic acid is also known as cis-9-Octadecenoic Acid, and is available from Natural Oleo Chemicals. It is an unsaturated fatty acid found in the lipid-rich cell membrane complex of healthy hair.

A. Cationic Surfactant System

The hair care composition described herein comprises a cationic surfactant system. The cationic surfactant system can be one cationic surfactant or a mixture of two or more cationic surfactants. The cationic surfactant system can be selected from: mono-long alkyl quaternized ammonium salt; a combination of mono-long alkyl quaternized ammonium salt and di-long alkyl quaternized ammonium salt; mono-long alkyl amidoamine salt; a combination of mono-long alkyl amidoamine salt and di-long alkyl quaternized ammonium salt, a combination of mono-long alkyl amidoamine salt and mono-long alkyl quaternized ammonium salt.

The cationic surfactant system can be included in the hair care composition at a level of from about 0.1% to about 10%, alternatively from about 0.5% to about 8%, alternatively from about 0.8% to about 5%, and alternatively from about 1.0% to about 4%, by weight of the hair care composition.

Mono-Long Alkyl Quaternized Ammonium Salt

The monoalkyl quaternized ammonium salt cationic surfactants useful herein are those having one long alkyl chain which has from 12 to 30 carbon atoms, from 16 to 24 carbon atoms, and in one embodiment at C18-22 alkyl group. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Mono-long alkyl quaternized ammonium salts useful herein are those having the formula (I):

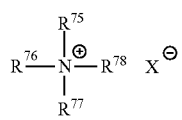

(I)

wherein one of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. One of $R^{75}$, $R^{76}$, $R^{77}$ and $R^{78}$ can be selected from an alkyl group of from 12 to 30 carbon atoms, from 16 to 24 carbon atoms, from 18 to 22 carbon atoms, an/or 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Nonlimiting examples of such mono-long alkyl quaternized ammonium salt cationic surfactants include: behenyl trimethyl ammonium salt; stearyl trimethyl ammonium salt; cetyl trimethyl ammonium salt; and hydrogenated tallow alkyl trimethyl ammonium salt.

Mono-Long Alkyl Amidoamine Salt

Mono-long alkyl amines are also suitable as cationic surfactants. Primary, secondary, and tertiary fatty amines are useful. Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Useful amines in the present invention are disclosed in U.S. Pat. No. 4,275,055, Nachtigal, et al. These amines can also be used in combination with acids such as ℓ-glutamic acid, lactic acid, hydrochloric acid, malic acid, succinic acid, acetic acid, fumaric acid, tartaric acid, citric acid, ℓ-glutamic hydrochloride, maleic acid, and mixtures thereof; in one embodiment ℓ-glutamic acid, lactic acid, and/or citric acid. The amines herein can be partially neutralized with any of the acids at a molar ratio of the amine to the acid of from about 1:0.3 to about 1:2, and/or from about 1:0.4 to about 1:1.

Di-Long Alkyl Quaternized Ammonium Salt

Di-long alkyl quaternized ammonium salt can be combined with a mono-long alkyl quaternized ammonium salt or mono-long alkyl amidoamine salt. It is believed that such combination can provide easy-to-rinse feel, compared to single use of a monoalkyl quaternized ammonium salt or mono-long alkyl amidoamine salt. In such combination with a mono-long alkyl quaternized ammonium salt or mono-long alkyl amidoamine salt, the di-long alkyl quaternized ammonium salts are used at a level such that the wt % of the dialkyl quaternized ammonium salt in the cationic surfactant system is in the range of from about 10% to about 50%, and/or from about 30% to about 45%.

The dialkyl quaternized ammonium salt cationic surfactants useful herein are those having two long alkyl chains having 12-30 carbon atoms, and/or 16-24 carbon atoms, and/or 18-22 carbon atoms. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Di-long alkyl quaternized ammonium salts useful herein are those having the formula (II):

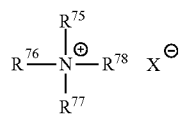

(II)

wherein two of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. One of $R^{75}$, $R^{76}$, $R^{77}$ and $R^{78}$ can be selected from an alkyl group of from 12 to 30 carbon atoms, from 16 to 24 carbon atoms, from 18 to 22 carbon atoms, and/or 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Such dialkyl quaternized ammonium salt cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride. Such dialkyl quaternized ammonium salt cationic surfactants also include, for example, asymmetric dialkyl quaternized ammonium salt cationic surfactants.

B. High Melting Point Fatty Compound

The hair care composition comprises one or more high melting point fatty compounds. The one or more high melting point fatty compounds useful herein can have a melting point of 25° C. or higher, and can be selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain carbon atoms may have a melting point of less than 25° C. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols are suitable for use in the hair care composition. The fatty alcohols useful herein are those having from about 14 to about 30 carbon atoms, from about 16 to about 22 carbon atoms. These fatty alcohols are saturated and can be straight or branched chain alcohols. Suitable fatty alcohols include, for example, cetyl alcohol, stearyl alcohol, behenyl alcohol, and mixtures thereof.

High melting point fatty compounds of a single compound of high purity can be used. Single compounds of pure fatty alcohols selected from the group of pure cetyl alcohol, stearyl alcohol, and behenyl alcohol can also be used. By "pure" herein, what is meant is that the compound has a purity of at least about 90%, and/or at least about 95%. These single compounds of high purity provide good rinsability from the hair when the consumer rinses off the composition.

The one or more high melting point fatty compounds can be included in the hair care composition at a level of from about 0.1% to about 20%, alternatively from about 1% to about 15%, and alternatively from about 1.5% to about 8%, by weight of the hair care. The one or more high melting point fatty compounds can provide improved conditioning benefits such as slippery feel during the application of the hair care composition to wet hair, hair softness on dry hair, and moisturized feel on dry hair.

C. Aqueous Carrier

The hair care composition comprises an aqueous carrier at a level of from about 75% to about 98%, alternatively from about 80% to about 95%, by weight of the hair care composition. Accordingly, the hair care composition can be in the form of pourable liquids (under ambient conditions). The aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The aqueous carrier can include water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

The hair care composition may have a pH in the range from about 2 to about 10, alternatively from about 3 to about 8, at 25° C. The hair care composition can also be effective toward washing out the existing minerals and redox metals deposits, which can reduce cuticle distortion and thereby reduce cuticle chipping and damage.

D. Gel Matrix

The hair care composition can comprise a gel matrix. The gel matrix comprises a cationic surfactant, a high melting point fatty compound, and an aqueous carrier.

The gel matrix is suitable for providing various conditioning benefits such as slippery feel during the application to wet hair and softness and moisturized feel on dry hair. In view of providing the above gel matrix, the cationic surfactant and the high melting point fatty compound are contained at a level such that the weight ratio of the cationic surfactant to the high melting point fatty compound is in the range of, from about 1:1 to about 1:10, and/or from about 1:1 to about 1:6.

E. Additional Components

1. Silicone Conditioning Agent

The hair care composition can include a silicone conditioning agent which comprises a silicone compound. The silicone compound may comprise volatile silicone, non-volatile silicones, or combinations thereof. If volatile silicones are present, it will typically be incidental to their use as a solvent or carrier for commercially available forms of non-volatile silicone materials ingredients, such as silicone gums and resins. The silicone compounds may comprise a silicone fluid conditioning agent and may also comprise other ingredients, such as a silicone resin to improve silicone fluid deposition efficiency or enhance glossiness of the hair. The concentration of the silicone compound in the hair care composition typically ranges from about 0.01 wt % to about 10 wt %, from about 0.1 wt % to about 8 wt %, from about 0.1 wt % to about 5 wt %, or even from about 0.2 wt % to about 3 wt %. Suitable silicones for use herein include, but are not limited to PDMS (Dimethicone) silicones, PQAS (Silicone Quaternium-26); PDMS, terminal aminosilicone, and combinations thereof.

Additional suitable silicone compounds include (a) a first polysiloxane which is non-volatile, substantially free of amino groups, and has a viscosity of from about 100,000 $mm^2s^{-1}$ to about 30,000,000 $mm^2s^{-1}$; (b) a second polysiloxane which is non-volatile, substantially free of amino groups, and has a viscosity of from about 5 $mm^2s^{-1}$ to about 10,000 $mm^2s^{-1}$; (c) an aminosilicone having less than about 0.5 wt % nitrogen by weight of the aminosilicone; (d) a silicone copolymer emulsion with an internal phase viscosity of greater than about $100 \times 10^6$ $mm^2s^{-1}$, as measured at 25° C.; (e) a silicone polymer containing quaternary groups; or (f) a grafted silicone polyol, wherein the silicone compounds (a)-(f) are disclosed in U.S. Patent Application Publication Nos. 2008/0292574, 2007/0041929, 2008/0292575, and 2007/0286837, each of which is incorporated by reference herein in its entirety.

a. First Polysiloxane

The hair care composition may comprise a first polysiloxane. The first polysiloxane is non-volatile, and substantially free of amino groups. The first polysiloxanes being "substantially free of amino groups" can mean that the first polysiloxane contains 0 wt % of amino groups. The first polysiloxane has a viscosity of from about 100,000 mm$^2$s$^{-1}$ to about 30,000,000 mm$^2$s$^{-1}$ at 25° C. For example, the viscosity may range from about 300,000 mm$^2$s$^{-1}$ to about 25,000,000 mm$^2$s$^{-1}$, or from about 10,000,000 mm$^2$s$^{-1}$ to about 20,000,000 mm$^2$s$^{-1}$. The first polysiloxane has a molecular weight from about 100,000 to about 1,000,000. For example, the molecular weight may range from about 130,000 to about 800,000, or from about 230,000 to about 600,000. According to one aspect, the first polysiloxane may be nonionic.

Exemplary first non-volatile polysiloxanes useful herein include those in accordance with the following the general formula (I):

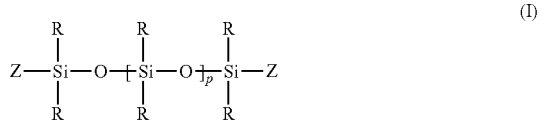

(I)

wherein R is alkyl or aryl, and p is an integer from about 1,300 to about 15,000, such as from about 1,700 to about 11,000, or from about 3,000 to about 8,000. Z represents groups which block the ends of the silicone chains. The alkyl or aryl groups substituted on the siloxane chain (R) or at the ends of the siloxane chains Z can have any structure as long as the resulting silicone remains fluid at room temperature, is dispersible, is neither irritating, toxic nor otherwise harmful when applied to the hair, is compatible with the other components of the composition, is chemically stable under normal use and storage conditions, and is capable of being deposited on and conditions the hair. Suitable Z groups include hydroxy, methyl, methoxy, ethoxy, propoxy, and aryloxy. The two R groups on each silicon atom may represent the same group or different groups. The two R groups may represent the same group. Suitable R groups include methyl, ethyl, propyl, phenyl, methylphenyl and phenylmethyl. Exemplary silicone compounds include polydimethylsiloxane, polydiethylsiloxane, and polymethylphenylsiloxane. Polydimethylsiloxane can be the first polysiloxane. Commercially available silicone compounds useful herein include, for example, those available from the General Electric Company in their TSF451 series, and those available from Dow Corning in their Dow Corning SH200 series.

The silicone compounds that can be used herein also include a silicone gum. The term "silicone gum", as used herein, means a polyorganosiloxane material having a viscosity at 25° C. of greater than or equal to 1,000,000 mm$^2$s$^{-1}$. It is recognized that the silicone gums described herein can also have some overlap with the above-disclosed silicone compounds. This overlap is not intended as a limitation on any of these materials. The "silicone gums" will typically have a mass molecular weight in excess of about 165,000, generally between about 165,000 and about 1,000,000. Specific examples include polydimethylsiloxane, poly(dimethylsiloxane methylvinylsiloxane) copolymer, poly(dimethylsiloxane diphenylsiloxane methylvinylsiloxane) copolymer and mixtures thereof. Commercially available silicone gums useful herein include, for example, TSE200A available from the General Electric Company.

b. Second Polysiloxane

The hair care composition may comprise a second polysiloxane. The second polysiloxane is non-volatile, and substantially free of amino groups. In the present invention, the second polysiloxane being "substantially free of amino groups" means that the second polysiloxane contains 0 wt % of amino groups. The second polysiloxane has a viscosity of from about 5 mm$^2$s$^{-1}$ to about 10,000 mm$^2$s$^{-1}$ at 25° C., such as from about 5 mm$^2$s$^{-1}$ to about 5,000 mm$^2$s$^{-1}$, from about 10 mm$^2$s$^{-1}$ to about 1,000 mm$^2$s$^{-1}$, or from about 20 mm$^2$s$^{-1}$ to about 350 mm$^2$s$^{-1}$. The second polysiloxane has a molecular weight of from about 400 to about 65,000. For example, the molecular weight of the second polysiloxane may range from about 800 to about 50,000, from about 400 to about 30,000, or from about 400 to about 15,000. According to one aspect, the second polysiloxane may be nonionic. According to another aspect, the second polysiloxane may be a linear silicone.

Exemplary second non-volatile polysiloxanes useful herein include polyalkyl or polyaryl siloxanes in accordance with the following the general formula (II):

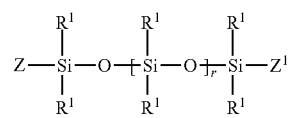

(II)

wherein $R^1$ is alkyl or aryl, and r is an integer from about 7 to about 850, such as from about 7 to about 665, from about 7 to about 400, or from about 7 to about 200. $Z^1$ represents groups which block the ends of the silicone chains. The alkyl or aryl groups substituted on the siloxane chain ($R^1$) or at the ends of the siloxane chains $Z^1$ can have any structure as long as the resulting silicone remains fluid at room temperature, is dispersible, is neither irritating, toxic nor otherwise harmful when applied to the hair, is compatible with the other components of the composition, is chemically stable under normal use and storage conditions, and is capable of being deposited on and conditions the hair. Suitable $Z^1$ groups include hydroxy, methyl, methoxy, ethoxy, propoxy, and aryloxy. The two $R^1$ groups on each silicon atom may represent the same group or different groups. The two $R^1$ groups may represent the same group. Suitable $R^1$ groups include methyl, ethyl, propyl, phenyl, methylphenyl and phenylmethyl. Exemplary silicone compounds include polydimethylsiloxane, polydiethylsiloxane, and polymethylphenylsiloxane. Polydimethylsiloxane can be the second polysiloxane. Commercially available silicone compounds useful herein include, for example, those available from the General Electric Company in their TSF451 series, and those available from Dow Corning in their Dow Corning SH200 series.

c. Aminosilicone

The hair care composition may comprise an amino silicone having less than about 0.5 wt % nitrogen by weight of the aminosilicone, such as less than about 0.2 wt %, or less than about 0.1 wt %, in view of friction reduction benefit. It has been surprisingly found that higher levels of nitrogen (amine functional groups) in the amino silicone tend to result in less friction reduction, and consequently less conditioning benefit from the aminosilicone. The aminosilicone useful herein may have at least one silicone block with greater than 200 siloxane units, in view of friction reduction benefit. The aminosilicones useful herein include, for example, quaternized aminosilicone and non-quaternized aminosilicone.

The aminosilicones useful herein are water-insoluble. "Water-insoluble aminosilicone" means that the aminosilicone has a solubility of 10 g or less per 100 g water at 25° C., alternatively 5 g or less per 100 g water at 25° C., and alternatively 1 g or less per 100 g water at 25° C. "Water-insoluble aminosilicone" means that the aminosilicone is substantially free of copolyol groups. If copolyol groups are present, they are present at a level of less than 10 wt %, less than 1 wt %, or less than 0.1 wt % by weight of the aminosilicone.

Aminosilicones useful herein are those which conform to the general formula (III):

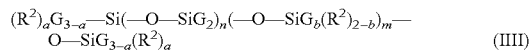

wherein G is hydrogen, phenyl, hydroxy, or $C_1$-$C_8$ alkyl, such as methyl; a is an integer having a value from 1 to 3, such as 1; b is an integer having a value from 0 to 2, such as 1; n is a number from 1 to 2,000, such as from 100 to 1,800, from 300 to 800, or from 500 to 600; m is an integer having a value from 0 to 1,999, such as from 0 to 10, or 0; $R^2$ is a monovalent radical conforming to the general formula $C_qH_{2q}L$, wherein q is an integer having a value from 2 to 8 and L is selected from the following groups: $-N(R^3_2)$; $CH_2-CH_2-N(R^3_2)_2$; $-N(R^3)_2$; $-N^+(R^3)_3A^-$; $-N(R^3)$ $CH_2-CH_2-N^+R^3H_2A^-$; wherein $R^3$ is hydrogen, phenyl, benzyl, or a saturated hydrocarbon radical, such as an alkyl radical from about $C_1$ to about $C_{20}$; $A^-$ is a halide ion. L can be $-N(CH_3)_2$ or $-NH_2$. Alternatively, L can be $-NH_2$.

The aminosilicone of the above formula is used at levels by weight of the composition of from about 0.1 wt % to about 5 wt %, alternatively from about 0.2 wt % to about 2 wt %, alternatively from about 0.2 wt % to about 1.0 wt %, and alternatively from about 0.3 wt % to about 0.8 wt %.

The aminosilicone may include those compounds corresponding to formula (III) wherein m=0; a=1; q=3; G=methyl; n is from about 1400 to about 1700, such as about 1600; and L is $-N(CH_3)_2$ or $-NH_2$, such as $-NH_2$. The aminosilicone may include those compounds corresponding to formula (III) wherein m=0; a=1; q=3; G=methyl; n is from about 400 to about 800, such as from about 500 to around 600; and L is L is $-N(CH_3)_2$ or $-NH_2$, such as $-NH_2$. Accordingly, the aforementioned aminosilicones can be called terminal aminosilicones, as one or both ends of the silicone chain are terminated by nitrogen containing group. Such terminal aminosilicones may provide improved friction reduction compared to graft aminosilicones.

Another example of an aminosilicone useful herein includes, for example, quaternized aminosilicone having a tradename KF8020 available from Shinetsu.

The above aminosilicones, when incorporated into the hair care composition, can be mixed with solvent having a lower viscosity. Such solvents include, for example, polar or non-polar, volatile or non-volatile oils. Such oils include, for example, silicone oils, hydrocarbons, and esters. Among such a variety of solvents, exemplary solvents include those selected from the group consisting of non-polar, volatile hydrocarbons, volatile cyclic silicones, non-volatile linear silicones, and mixtures thereof. The non-volatile linear silicones useful herein are those having a viscosity of from about 1 $mm^2s^{-1}$ to about 20,000 $mm^2s^{-1}$, such as from about 20 $mm^2s^{-1}$ to about 10,000 $mm^2s^{-1}$, at 25° C. The solvents may be non-polar, volatile hydrocarbons, especially non-polar, volatile isoparaffins, in view of reducing the viscosity of the aminosilicones and providing improved hair conditioning benefits such as reduced friction on dry hair. Such mixtures may have a viscosity of from about 1,000 mPa·s to about 100,000 mPa·s, and alternatively from about 5,000 mPa·s to about 50,000 mPa·s.

d. Silicone Copolymer Emulsion

The hair care composition may comprise a silicone copolymer emulsion with an internal phase viscosity of greater than about $100\times10^6$ $mm^2s^{-1}$. The silicone copolymer emulsion may be present in an amount of from about 0.1 wt % to about 15 wt %, alternatively from about 0.3 wt % to about 10 wt %, and alternatively about 0.5 wt % to about 5 wt %, by weight of the composition, in view of providing clean feel.

The silicone copolymer emulsion can have a viscosity at 25° C. of greater than about $100\times10^6$ $mm^2s^{-1}$, alternatively greater than about $120\times10^6$ $mm^2s^{-1}$, and alternatively greater than about $150\times10^6$ $mm^2s^{-1}$. Alternatively, the silicone copolymer emulsion has a viscosity at 25° C. of less than about $1000\times10^6$ $mm^2s^{-1}$, alternatively less than about $500\times10^6$ $mm^2s^{-1}$, and alternatively less than about $300\times10^6$ $mm^2s^{-1}$. To measure the internal phase viscosity of the silicone copolymer emulsion, one may first break the polymer from the emulsion. By way of example, the following procedure can be used to break the polymer from the emulsion: 1) add 10 grams of an emulsion sample to 15 milliliters of isopropyl alcohol; 2) mix well with a spatula; 3) decant the isopropyl alcohol; 4) add 10 milliliters of acetone and knead polymer with spatula; 5) decant the acetone; 6) place polymer in an aluminum container and flatten/dry with a paper towel; and 7) dry for two hours in an 80° C. The polymer can then be tested using any known rheometer, such as, for example, a CarriMed, Haake, or Monsanto rheometer, which operates in the dynamic shear mode. The internal phase viscosity values can be obtained by recording the dynamic viscosity (n') at a $9.900*10^{-3}$ Hz frequency point. The average particle size of the emulsions can be less than about 1 micron, such as less than about 0.7 micron.

The silicone copolymer emulsions of the present invention may comprise a silicone copolymer, at least one surfactant, and water.

The silicone copolymer results from the addition reaction of the following two materials in the presence of a metal containing catalyst:

(i) a polysiloxane with reactive groups on both termini, represented by a general formula (IV):

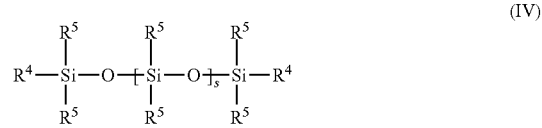

wherein:

$R^4$ is a group capable of reacting by chain addition reaction such as, for example, a hydrogen atom, an aliphatic group with ethylenic unsaturation (i.e., vinyl, allyl, or hexenyl), a hydroxyl group, an alkoxyl group (i.e., methoxy, ethoxy, or propoxy), an acetoxyl group, or an amino or alkylamino group;

$R^5$ is alkyl, cycloalkyl, aryl, or alkylaryl and may include additional functional groups such as ethers, hydroxyls, amines, carboxyls, thiols esters, and sulfonates; and $R^5$ can be methyl. Optionally, a small mole percentage of the groups may be reactive groups as described above for $R^5$, to produce a polymer which is substantially linear but with a small amount of branching. In this case, the level of $R^5$ groups equivalent to $R^4$ groups may be less than about 10% on a mole percentage basis, such as less than about 2%; s is an integer having a value such that the polysiloxane of formula (IV) has a viscosity of from about 1 $mm^2s^{-1}$ to about $1\times10^6$ $mm^2s^{-1}$;

and, (ii) at least one silicone compound or non-silicone compound comprising at least one or at most two groups capable of reacting with the $R^4$ groups of the polysiloxane in formula (IV). The reactive group can be an aliphatic group with ethylenic unsaturation.

The metal containing catalysts used in the above described reactions are often specific to the particular reaction. Such catalysts are known in the art. Generally, they are materials containing metals such as platinum, rhodium, tin, titanium, copper, lead, etc.

The mixture used to form the emulsion also may contain at least one surfactant. This can include non-ionic surfactants, cationic surfactants, anionic surfactants, alkylpolysaccharides, amphoteric surfactants, and the like. The above surfactants can be used individually or in combination.

An exemplary method of making the silicone copolymer emulsions described herein comprises the steps of 1) mixing materials (a) described above with material (b) described above, followed by mixing in an appropriate metal containing catalyst, such that material (b) is capable of reacting with material (a) in the presence of the metal containing catalyst; 2) further mixing in at least one surfactant and water; and 3) emulsifying the mixture. Methods of making such silicone copolymer emulsions are disclosed in U.S. Pat. No. 6,013,682; PCT Application No. WO 01/58986 A1; and European Patent Application No. EP0874017 A2.

A commercially available example of a silicone copolymer emulsion is an emulsion of about 60-70 wt % of divinyldimethicone/dimethicone copolymer having an internal phase viscosity of minimum $120\times10^6$ $mm^2s^{-1}$, available from Dow Corning with a tradename HMW2220.

e. Silicone Polymer Containing Quaternary Groups

The hair care composition may comprise a silicone polymer containing quaternary groups (i.e., a quaternized silicone polymer). The quaternized silicone polymer provides improved conditioning benefits such as smooth feel, reduced friction, prevention of hair damage. Especially, the quaternary group can have good affinity with damaged/colorant hairs. The quaternized silicone polymer is present in an amount of from about 0.1 wt % to about 15 wt %, based on the total weight of the hair conditioning composition. For example, the quaternized silicone polymer may be present in an amount from about 0.2 wt % to about 10 wt %, alternatively from about 0.3 wt % to about 5 wt %, and alternatively from about 0.5 wt % to about 4 wt %, by weight of the composition.

The quaternized silicone polymer of the present invention is comprised of at least one silicone block and at least one non-silicone block containing quaternary nitrogen groups, wherein the number of the non-silicone blocks is one greater than the number of the silicone blocks. The silicone polymers correspond to the general structure (V):

wherein, B is a silicone block having greater than 200 siloxane units; $A^1$ is an end group which may contain quaternary groups; $A^2$ is a non-silicone blocks containing quaternary nitrogen groups; and m is an integer 0 or greater, with the proviso that if m=0 then the $A^1$ group contains quaternary groups.

Structures corresponding to the general formula, for example, are disclosed in U.S. Pat. No. 4,833,225, in U.S. Patent Application Publication No. 2004/0138400, in U.S. Patent Application Publication No. 2004/0048996, and in U.S. Patent Application Publication No. 2008/0292575.

The silicone polymers can be represented by the following structure (VI)

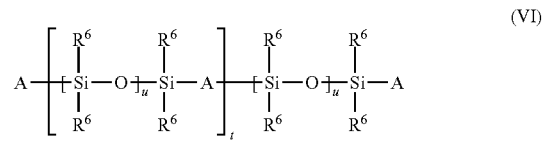

wherein, A is a group which contains at least one quaternary nitrogen group, and which is linked to the silicon atoms of the silicone block by a silicon-carbon bond, each A independently can be the same or different; $R^6$ is an alkyl group of from about 1 to about 22 carbon atoms or an aryl group; each $R^6$ independently can be the same or different; t is an integer having a value of from 0 or greater, for example t can be less than 20, or less than 10; and u is an integer greater than about 200, such as greater than about 250, or greater than about 300, and u may be less than about 700, or less than about 500. The $R^6$ can be methyl.

f. Grafted Silicone Copolyol

The hair care composition may comprise a grafted silicone copolyol in combination with the quaternized silicone polymer. It is believed that this grafted silicone copolyol can improve the spreadability of the quaternized silicone polymer by reducing the viscosity of the quaternized silicone polymer, and also can stabilize the quaternized silicone polymer in aqueous conditioner matrix. It is also believed that, by such improved spreadability, the hair care compositions of the present invention can provide better dry conditioning benefits such as friction reduction and/or prevention of damage with reduced tacky feel. It has been surprisingly found that the combination of the quaternized silicone polymer, grafted silicone copolyol, and cationic surfactant system comprising di-alkyl quaternized ammonium salt cationic surfactants provides improved friction reduction benefit, compared to a similar combination. Such similar combinations are, for example, a combination in which the grafted silicone copolyol is replaced with end-capped silicone copolyol, and another combination in which the cationic surfactant system is substantially free of di-alkyl quaternized ammonium salt cationic surfactants.

The grafted silicone copolyol is contained in the composition at a level such that the weight % of the grafted silicone copolyol to its mixture with quaternized silicone copolymer is in the range of from about 1 wt % to about 50 wt %, alternatively from about 5 wt % to about 40 wt %, and alternatively from about 10 wt % to 30 wt %.

The grafted silicone copolyols useful herein are those having a silicone backbone such as dimethicone backbone and polyoxyalkylene substitutions such as polyethylene oxide and/or polypropylene oxide substitutions. The grafted silicone copolyols useful herein have a hydrophilic-lipophilic balance (HLB) value of from about 5 to about 17, such as from about 8 to about 17, or from about 8 to about 12. The grafted silicone copolyols having the same INCI name have a variety of the weight ratio, depending on the molecular weight of the silicone portion and the number of the polyethylene oxide and/or polypropylene oxide substitutions.

Suitable commercially available grafted dimethicone copolyols include, for example: those having a tradename Silsoft 430 having an HLB value of from about 9 to about 12 (INCI name "PEG/PPG-20/23 dimethicone") available from GE; those having a tradename Silsoft 475 having an HLB value of from about 13 to about 17 (INCI name "PEG-23/PPG-6 dimethicone"); those having a tradename Silsoft 880 having an HLB value of from about 13 to about 17 (INCI name "PEG-12 dimethicone"); those having a tradename Silsoft 440 having an HLB value of from about 9 to about 12 (INCI name "PEG-20/PPG-23 dimethicone"); those having a tradename DC5330 (INCI name "PEG-15/PPG-15 dimethicone") available from Dow Corning.

The above quaternized silicone polymer and the grafted silicone copolyol may be mixed and emulsified by a emulsifying surfactant, prior to incorporating them into a gel matrix formed by cationic surfactants and high melting point fatty compounds, as discussed below. It is believed that, this pre-mixture can improve behavior of the quaternized silicone polymer and the grafted silicone copolyol, for example, increase the stability and reduce the viscosity to form more homogenized formulation together with the other components. Such emulsifying surfactant can be used at a level of about 0.001 wt % to about 1.5 wt %, alternatively from about 0.005% to about 1.0%, and alternatively from about 0.01 wt % to about 0.5 wt %, based on the total weight of the hair conditioning composition. Such surfactants may be nonionic, and have an HLB value of from about 2 to about 15, such as from about 3 to about 14, or from about 3 to about 10. Commercially available examples of emulsifying surfactant include nonionic surfactants having an INCI name C12-C14 Pareth-3 and having an HLB value of about 8 supplied from NIKKO Chemicals Co., Ltd. with tradename NIKKOL BT-3.

The hair care composition can comprise a combination of two or more silicone conditioning agents, along with an EDDS sequestering agent and a gel matrix.

The hair care composition can comprise a polyalkylsiloxane mixture comprising (i) a first polyalkylsiloxane which is non-volatile, substantially free of amino groups, and has a viscosity of from about 100,000 $mm^2s^{-1}$ to about 30,000,000 $mm^2s^{-1}$, and (ii) a second polyalkylsiloxane which is non-volatile, substantially free of amino groups, and has a viscosity of from about 5 $mm^2s^{-1}$ to about 10,000 $mm^2s^{-1}$; an aminosilicone having less than about 0.5 wt % nitrogen by weight of the aminosilicone; and a silicone copolymer emulsion with an internal phase viscosity of greater than about $100 \times 10^6$ $mm^2s^{-1}$, as measured at 25° C. For example, the hair care composition can comprise from about 0.5 wt % to about 10 wt % of a polyalkylsiloxane mixture comprising (i) a first polyalkylsiloxane which is non-volatile, substantially free of amino groups, and has a viscosity of from about 100,000 $mm^2s^{-1}$ to about 30,000,000 $mm^2s^{-1}$, and (ii) a second polyalkylsiloxane which is non-volatile, substantially free of amino groups, and has a viscosity of from about 5 $mm^2s^{-1}$ to about 10,000 $mm^2s^{-1}$; from about 0.1 wt % to about 5 wt % of an aminosilicone having less than about 0.5 wt % nitrogen by weight of the aminosilicone; and from about 0.1 wt % to about 5 wt % of a silicone copolymer emulsion with an internal phase viscosity of greater than about $100 \times 10^6$ $mm^2s^{-1}$, as measured at 25° C.

The hair care composition can comprise a silicone polymer containing quaternary groups wherein said silicone polymer comprises silicone blocks with greater than about 200 siloxane units; and a grafted silicone copolyol. For example, the hair care composition can comprise from about 0.1 wt % to about 15 wt % of a silicone polymer containing quaternary groups wherein said silicone polymer comprises silicone blocks with greater than about 200 siloxane units; and a grafted silicone copolyol at a level such that the weight % of the grafted silicone copolyol in its mixture with the quaternized silicone polymer is in the range of from about 1 wt % to about 50 wt %.

The hair care composition can comprise an aminosilicone having a viscosity of from about 1,000 centistokes to about 1,000,000 centistokes, and less than about 0.5% nitrogen by weight of the aminosilicone; and (2) a silicone copolymer emulsion with an internal phase viscosity of greater than about $120 \times 10^6$ centistokes, as measured at 25° C.

2. Other Conditioning Agents

Also suitable for use in the hair care compositions herein are the conditioning agents described by the Procter & Gamble Company in U.S. Pat. Nos. 5,674,478, and 5,750,122. Also suitable for use herein are those conditioning agents described in U.S. Pat. Nos. 4,529,586, 4,507,280, 4,663,158, 4,197,865, 4,217, 914, 4,381,919, and 4,422,853.

a. Organic Conditioning Oils

The hair care composition may also further comprise an organic conditioning oil. The hair care composition may comprise from about 0.05 wt % to about 3 wt %, from about 0.08 wt % to about 1.5 wt %, or even from about 0.1 wt % to about 1 wt %, of at least one organic conditioning oil as the conditioning agent, in combination with other conditioning agents, such as the silicones (described herein). Suitable conditioning oils include hydrocarbon oils, polyolefins, and fatty esters. Suitable hydrocarbon oils include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils are typically from about C12 to about C19. Branched chain hydrocarbon oils, including hydrocarbon polymers, typically will contain more than 19 carbon atoms. Suitable polyolefins include liquid polyolefins, liquid poly-α-olefins, or even hydrogenated liquid poly-α-olefins. Polyolefins for use herein may be prepared by polymerization of C4 to about C14 or even C6 to about C12. Suitable fatty esters include, but are not limited to, fatty esters having at least 10 carbon atoms. These fatty esters include esters with hydrocarbyl chains derived from fatty acids or alcohols (e.g. mono-esters, polyhydric alcohol esters, and di- and tri-carboxylic acid esters). The hydrocarbyl radicals of the fatty esters hereof may include or have covalently bonded thereto other compatible functionalities, such as amides and alkoxy moieties (e.g., ethoxy or ether linkages, etc.).

3. Nonionic Polymers

The hair care composition may also further comprise a nonionic polymer. The conditioning agent for use in the hair care composition of the present invention may include a polyalkylene glycol polymer. For example, polyalkylene glycols having a molecular weight of more than about 1000 are useful herein. Useful are those having the following general formula (VIII):

wherein $R^{11}$ is selected from the group consisting of H, methyl, and mixtures thereof; and v is the number of ethoxy units. The polyalkylene glycols, such as polyethylene glycols, can be included in the hair care compositions of the present invention at a level of from about 0.001 wt % to about 10 wt %. The polyethylene glycol can be present in an amount up to about 5 wt % based on the weight of the composition. Polyethylene glycol polymers useful herein are PEG-2M (also known as Polyox WSR® N-10, which is available from Union Carbide and as PEG-2,000); PEG-5M (also known as Polyox WSR® N-35 and Polyox WSR® N-80, available from Union Carbide and as PEG-5,000 and Polyethylene Glycol 300,000); PEG-7M (also known as Polyox WSR® N-750 available from Union Carbide); PEG-9M (also known as Polyox WSR® N-3333 available from Union Carbide); and PEG-14 M (also known as Polyox WSR® N-3000 available from Union Carbide).

4. Suspending Agent

The hair care composition may further comprise a suspending agent at concentrations effective for suspending water-insoluble material in dispersed form in the compositions or for modifying the viscosity of the composition. Such concentrations range from about 0.1 wt % to about 10 wt %, or even from about 0.3 wt % to about 5.0 wt %.

Suspending agents useful herein include anionic polymers and nonionic polymers. Useful herein are vinyl polymers such as cross linked acrylic acid polymers with the CTFA name Carbomer, cellulose derivatives and modified cellulose polymers such as methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabia gum, tragacanth, galactan, carob gum, guar gum, karaya gum, carrageenan, pectin, agar, quince seed (Cydonia oblonga Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate, alginic acid propylene glycol esters, acrylate polymers such as sodium polyacrylate, polyethylacrylate, polyacrylamide, polyethyleneimine, and inorganic water soluble material such as bentonite, aluminum magnesium silicate, laponite, hectonite, and anhydrous silicic acid.

Commercially available viscosity modifiers highly useful herein include Carbomers with trade names Carbopol® 934, Carbopol® 940, Carbopol® 950, Carbopol® 980, and Carbopol® 981, all available from B. F. Goodrich Company, acrylates/steareth-20 methacrylate copolymer with trade name ACRYSOL™ 22 available from Rohm and Hass, nonoxynyl hydroxyethylcellulose with trade name Amercell™POLYMER HM-1500 available from Amerchol, methylcellulose with trade name BENECEL®, hydroxyethyl cellulose with trade name NATROSOL®, hydroxypropyl cellulose with trade name KLUCEL®, cetyl hydroxyethyl cellulose with trade name POLYSURF® 67, all supplied by Hercules, ethylene oxide and/or propylene oxide based polymers with trade names CARBOWAX® PEGs, POLYOX™ WASRs, and UCON® FLUIDS, all supplied by Amerchol.

Other optional suspending agents include crystalline suspending agents which can be categorized as acyl derivatives, long chain amine oxides, and mixtures thereof. These suspending agents are described in U.S. Pat. No. 4,741,855.

These suspending agents include ethylene glycol esters of fatty acids in one aspect having from about 16 to about 22 carbon atoms. In one aspect, useful suspending agents include ethylene glycol stearates, both mono and distearate, but in one aspect, the distearate containing less than about 7% of the mono stearate. Other suitable suspending agents include alkanol amides of fatty acids, having from about 16 to about 22 carbon atoms, or even about 16 to 18 carbon atoms, examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); long chain esters of long chain alkanol amides (e.g., stearamide diethanolamide distearate, stearamide monoethanolamide stearate); and glyceryl esters (e.g., glyceryl distearate, trihydroxystearin, tribehenin) a commercial example of which is THIXCIN® R available from Rheox, Inc. Long chain acyl derivatives, ethylene glycol esters of long chain carboxylic acids, long chain amine oxides, and alkanol amides of long chain carboxylic acids in addition to the materials listed above may be used as suspending agents.

Other long chain acyl derivatives suitable for use as suspending agents include N,N-dihydrocarbyl amido benzoic acid and soluble salts thereof (e.g., Na, K), particularly N,N-di(hydrogenated) C16, C18 and tallow amido benzoic acid species of this family, which are commercially available from Stepan Company (Northfield, Ill., USA).

Examples of suitable long chain amine oxides for use as suspending agents include alkyl dimethyl amine oxides, e.g., stearyl dimethyl amine oxide.

Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow)amine. Still other suitable suspending agents include di(hydrogenated tallow)phthalic acid amide, and crosslinked maleic anhydride-methyl vinyl ether copolymer.

H. Benefit Agents

The hair care composition can further comprises one or more additional benefit agents. The benefit agents comprise a material selected from the group consisting of anti-dandruff agents, vitamins, lipid soluble vitamins, chelants, perfumes, brighteners, enzymes, sensates, attractants, anti-bacterial agents, dyes, pigments, bleaches, and mixtures thereof.

In one aspect said benefit agent may comprise an anti-dandruff agent. Such anti-dandruff particulate should be physically and chemically compatible with the components of the composition, and should not otherwise unduly impair product stability, aesthetics or performance.

The hair care composition can comprise an anti-dandruff active, which may be an anti-dandruff active particulate. The anti-dandruff active can be selected from the group consisting of: pyridinethione salts; azoles, such as ketoconazole, econazole, and elubiol; selenium sulphide; particulate sulfur; keratolytic agents such as salicylic acid; and mixtures thereof. The anti-dandruff particulate can be a pyridinethione salt.

Pyridinethione particulates are suitable particulate anti-dandruff actives. The anti-dandruff active can be a 1-hydroxy-2-pyridinethione salt and is in particulate form. The concentration of pyridinethione anti-dandruff particulate ranges from about 0.01 wt % to about 5 wt %, or from about 0.1 wt % to about 3 wt %, or from about 0.1 wt % to about 2 wt %. The pyridinethione salts are those formed from heavy metals such as zinc, tin, cadmium, magnesium, aluminium and zirconium, generally zinc, typically the zinc salt of 1-hydroxy-2-pyridinethione (known as "zinc pyridinethione" or "ZPT"), commonly 1-hydroxy-2-pyridinethione salts in platelet particle form. The 1-hydroxy-2-pyridinethione salts can be in platelet particle form have an average particle size of up to about 20 microns, or up to about 5 microns, or up to about 2.5 microns. Salts formed from other cations, such as sodium, may also be suitable. Pyridinethione anti-dandruff actives are described, for example, in U.S. Pat. Nos. 2,809,971; 3,236,733; 3,753,196; 3,761,418; 4,345,080; 4,323,683; 4,379,753; and 4,470,982.

In addition to the anti-dandruff active selected from polyvalent metal salts of pyrithione, the composition may further comprise one or more anti-fungal and/or anti-microbial actives. The anti-microbial active can be selected from the group consisting of: coal tar, sulfur, fcharcoal, whitfield's ointment, castellani's paint, aluminum chloride, gentian violet, octopirox (piroctone olamine), ciclopirox olamine, undecylenic acid and its metal salts, potassium permanganate, selenium sulphide, sodium thiosulfate, propylene glycol, oil of bitter orange, urea preparations, griseofulvin, 8-hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, SENSIVA® SC-50, ELESTAB ® HP-100, azelaic acid, lyticase, iodopropynyl butylcarbamate (IPBC), isothiazalinones such as octyl isothiazalinone, and azoles, and mixtures thereof. The anti-microbial can be selected from the group consisting of: itraconazole, ketoconazole, selenium sulphide, coal tar, and mixtures thereof.

The azole anti-microbials can be an imidazole selected from the group consisting of: benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and mixtures thereof, or the azole anti-microbials is a triazole selected from the group consisting of: terconazole, itraconazole, and mixtures thereof. When present in the hair care composition, the azole anti-microbial active can be included in an amount of from about 0.01 wt % to about 5 wt %, or from about 0.1 wt % to about 3 wt %, or from about 0.3 wt % to about 2 wt %. The azole anti-microbial active can be ketoconazole. The sole anti-microbial active can be ketoconazole.

Embodiments of the hair care composition may also comprise a combination of anti-microbial actives. The combination of anti-microbial active can be selected from the group of combinations consisting of: octopirox and zinc pyrithione, pine tar and sulfur, salicylic acid and zinc pyrithione, salicylic acid and elubiol, zinc pyrithione and elubiol, zinc pyrithione and climbasole, octopirox and climbasole, salicylic acid and octopirox, and mixtures thereof.

The hair care composition can comprise an effective amount of a zinc-containing layered material. The hair care composition can comprise from about 0.001 wt % to about 10 wt %, or from about 0.01 wt % to about 7 wt %, or from about 0.1 wt % to about 5 wt % of a zinc-containing layered material, by total weight of the hair care composition.

Zinc-containing layered materials may be those with crystal growth primarily occurring in two dimensions. It is conventional to describe layer structures as not only those in which all the atoms are incorporated in well-defined layers, but also those in which there are ions or molecules between the layers, called gallery ions (A. F. Wells "Structural Inorganic Chemistry" Clarendon Press, 1975). Zinc-containing layered materials (ZLMs) may have zinc incorporated in the layers and/or be components of the gallery ions. The following classes of ZLMs represent relatively common examples of the general category and are not intended to be limiting as to the broader scope of materials which fit this definition.

Many ZLMs occur naturally as minerals. The ZLM can be selected from the group consisting of: hydrozincite (zinc carbonate hydroxide), aurichalcite (zinc copper carbonate hydroxide), rosasite (copper zinc carbonate hydroxide), and mixtures thereof. Related minerals that are zinc-containing may also be included in the composition. Natural ZLMs can also occur wherein anionic layer species such as clay-type minerals (e.g., phyllosilicates) contain ion-exchanged zinc gallery ions. All of these natural materials can also be obtained synthetically or formed in situ in a composition or during a production process.

Another common class of ZLMs, which are often, but not always, synthetic, is layered double hydroxides. The ZLM can be a layered double hydroxide conforming to the formula $[M^{2+}_{1-x}M^{3+}_x(OH)_2]^{x+}A^{n-}_{x/m}\cdot nH_2O$ wherein some or all of the divalent ions ($M^{2+}$) are zinc ions (Crepaldi, E L, Pava, P C, Tronto, J, Valim, J B J. Colloid Interfac. Sci. 2002, 248, 429-42).

Yet another class of ZLMs can be prepared called hydroxy double salts (Morioka, H., Tagaya, H., Karasu, M, Kadokawa, J, Chiba, K Inorg. Chem. 1999, 38, 4211-6). The ZLM can be a hydroxy double salt conforming to the formula $[M^{2+}_{1-x}M^{2+}_{1+x}(OH)_{3(1-y)}]^+A^{n-}_{(1=3y)/n}\cdot nH_2O$ where the two metal ions ($M^{2+}$) may be the same or different. If they are the same and represented by zinc, the formula simplifies to $[Zn_{1+x}(OH)_2]^{2x+}2x\ A^-\cdot nH_2O$. This latter formula represents (where x=0.4) materials such as zinc hydroxychloride and zinc hydroxynitrate. The ZLM can be a zinc hydroxychloride and/or zinc hydroxynitrate. These are related to hydrozincite as well wherein a divalent anion replaces the monovalent anion. These materials can also be formed in situ in a composition or in or during a production process.

In products containing a zinc-containing layered material and a pyrithione or polyvalent metal salt of pyrithione, the ratio of zinc-containing layered material to pyrithione or a polyvalent metal salt of pyrithione is from about 5:100 to about 10:1, or from about 2:10 to about 5:1, or from about 1:2 to about 3:1.

The on-scalp deposition of the anti-dandruff active is at least about 1 microgram/cm$^2$. The on-scalp deposition of the anti-dandruff active is important in view of ensuring that the anti-dandruff active reaches the scalp where it is able to perform its function. The deposition of the anti-dandruff active on the scalp can be at least about 1.5 microgram/cm$^2$, or at least about 2.5 microgram/cm$^2$, or at least about 3 microgram/cm$^2$, or at least about 4 microgram/cm$^2$, or at least about 6 microgram/cm$^2$, or at least about 7 microgram/cm$^2$, or at least about 8 microgram/cm$^2$, or at least about 8 microgram/cm$^2$, or at least about 10 microgram/cm$^2$. The on-scalp deposition of the anti-dandruff active is measured by having the hair of individuals washed with a composition comprising an anti-dandruff active, for example a composition pursuant to the present invention, by trained a cosmetician according to a conventional washing protocol. The hair is then parted on an area of the scalp to allow an open-ended glass cylinder to be held on the surface while an aliquot of an extraction solution is added and agitated prior to recovery and analytical determination of anti-dandruff active content by conventional methodology, such as HPLC.

Product Forms

The compositions of the present invention can be in the form of rinse-off products or leave-on products, and can be formulated in a wide variety of product forms, including but not limited to creams, gels, emulsions, mousses and sprays. The composition of the present invention is especially suitable for conditioning compositions especially leave-on, leave-in, and/or no-rinse compositions. Leave-on and leave-in conditioning compositions are generally used on dry, semi-wet, and/or wet hair without rinsing out the composition. By no-rinse compositions, what is meant herein is a hair care composition used on semi-wet to wet hair after shampooing, without rinsing out the no-rise hair care composition (such as a no-rinse hair conditioner).

Test Method

Fatigue Measurements

Fibers are cut for fatigue strength measurements from the middle of the tress and ends crimped at 30 mm using a Dia-stron Auto-Assembly System (AAS 1600). The average cross-sectional area along each fiber, is analyzed using a Dia-Stron Fiber Dimensional Analysis System (FDAS 770), which incorporates a Mitutoyo laser micrometer (LSM-6200). The average cross-sectional area is calculated from three diameter measurement points along each 30 mm crimped fiber.

For fatigue strength the average cross-sectional values for each of the fibers are then used to set the Dia-Stron Cyclic Tester (CYC801) in controlled stress mode of 0.014 g/µm2 and rate of 40 mm/s. The relative humidity is set 50% RH and temperature at 23° C. Data is analyzed by Weibull and Kaplan-Meier statistical tools (JMP Pro 12.1.0, SAS Cary, N.C.). Fibers with break cycles less than ten are omitted from the analysis due to premature breakage. 100 fibers per leg are measured.

Sample Preparation

Sample solutions are prepared by dissolving Azelaic and/or Oleic Acid in water/ethanol at 0.0833% total acid and pH adjusted to approximately 4.5 with NaOH solution. These solutions are syringed onto 4 g/8" regular bleach (IHI sourced) hair switches (6 mL) and left to penetrate/dry at ambient room conditions. This produces hair dosed with 1.25 mg total acid/g hair.

Examples

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

| Smoothing Rinse-off Conditioner Compositions | |
|---|---|
| Components | Wt % |
| Stearyl alcohol | 2.32 |
| Cetyl alcohol | 0.93 |
| Dicetyldimonium chloride | 0.34 |
| Behentrimonium methosulfate | 1.16 |
| Propylene glycol | 0.16 |

| Smoothing Rinse-off Conditioner Compositions | |
|---|---|
| Components | Wt % |
| Isopropyl alcohol | 0.28 |
| Disodium EDTA Dihydrate | 0.13 |
| Terminal amodimethicone[1] | 0.75 |
| Azelaic acid | 1.00 |
| Oleic acid | 0.33 |
| Methylchloroisothiazolinone/Methylisothiazolinone[2] | 0.0005 |
| Benzyl alcohol | 0.40 |
| Distilled Water | Q.S. |

[1]Terminal amodimethicone with visc. Of 10,000 cP at 25° C. is available by Momentive Performance Materials.
[2]Kathon CG available from Dow (1.5 wt % active)

| Volumizing Rinse-off Conditioner Compositions | |
|---|---|
| Components | Wt % |
| Hydroxypropyl guar[1] | 0.35 |
| DTDMAC (Quaternium-18[2]) | 0.75 |
| Stearamidopropyldimethylamine | 1.00 |
| Glyceryl monostearate | 0.25 |
| Emulsifying wax NF (Polywax NF) | 0.50 |
| Cetyl alcohol | 1.20 |
| Stearyl alcohol | 0.80 |
| Oleyl alcohol | 0.25 |
| Citric acid | 0.13 |
| EDTA | 0.10 |
| Terminal amodimethicone[3] | 0.50 |
| Azelaic acid | 1.50 |
| Oleic acid | 0.50 |
| Methylchloroisothiazolinone/Methylisothiazolinone[4] | 0.0005 |
| Benzyl alcohol | 0.4 |
| Distilled Water | Q.S. |

[1]Jaguar HP-105 supplied by Rhodia
[2]Diatallowdimethylammonium chloride
[3]Terminal amodimethicone with visc. Of 10,000 cP at 25° C. is available by Momentive Performance Materials.
[4]Kathon CG available from Dow (1.5 wt % active).

| Hair Repair Rinse-off Conditioner Compositions | |
|---|---|
| Components | Wt % |
| Behentrimonium chloride | 2.28 |
| Stearyl alcohol | 4.64 |
| Cetyl alcohol | 0.93 |
| Isopropyl alcohol | 0.57 |
| Disodium EDTA Dihydrate | 0.13 |
| Dimethicone[1] | 4.20 |
| Sodium hydroxide | 0.02 |
| Azelaic acid | 1.00 |
| Oleic acid | 0.33 |
| Methylchloroisothiazolinone/Methylisothiazolinone[2] | 0.0005 |
| Benzyl alcohol | 0.40 |
| Distilled Water | Q.S. |

[1]Mixture of silicone gum and silicone oil XF49-B1747 available from Momentive Performance Materials.
[2]Kathon CG available from Dow (1.5 wt % active).

| Leave-on Treatment Composition | |
| --- | --- |
| Components | Wt % |
| Amodimethicone and Cetrimonium chloride and Trideceth-12[1] | 0.35 |
| Polyquaternium-11[2] | 0.75 |
| PEG-40 Hydrogenated castor oil | 0.50 |
| PPG-2 Methyl ether | 0.5 |
| DMDM Hydantoin | 0.20 |
| Disodium EDTA | 0.14 |
| Polysorbate 80 | 0.12 |
| Azelaic acid | 1.50 |
| Oleic acid | 0.50 |
| Aminomethyl propanol | 0.1 |
| Citric acid anhydrous | 0.08 |
| Distilled Water | Q.S. |

[1]Siameter MEM-0949 Emulsion available from Dow Corning; it contains 35% aminosilicone
[2]Copolymer of vinylpyrrolidone and quaternized dimethylaminoethyl methacrylate; Gafquat 755 NH available by Ashland

| Components | Wt % |
| --- | --- |
| Distilled Water | QS |
| Ethanol | 50.00 |
| Polyacrylamide & C13-14 Isoparaffin & Laureth-7 (Sepigel 305) | 1.85 |
| Perfume | 0.46 |
| Oleic acid | 1.00 |
| Azelaic acid | 0.33 |

| Components | Active % | Wt % |
| --- | --- | --- |
| Hydroxyethyl cellulose[1] | 80 | 0.400 |
| Cetyl Alcohol[2] | 90 | 0.575 |
| Stearyl Alcohol[3] | 97 | 0.383 |
| Benzyl Alcohol[4] | 99 | 0.400 |
| Disodium EDTA, Dihydrate[5] | 99 | 0.127 |
| Glyceryl monostearate (PoloxWSR N-10)[6] | 1.5 | 0.299 |
| Terminal Amino Silicone[7] | 90-100 | 2 |
| Perfume | | 0.550 |
| Oleic acid | 100 | 1.50 |
| Azelaic acid | 100 | 0.50 |
| Purified Water | | Q.S. |

[1]Natrosol ™ hydroxyethylcellulose Supplied by Ashland (Kentucky, US)
[2]Supplied by P&G Chemicals
[3]Supplied by P&G Chemicals
[4]Supplied by Ineos Maastricht BV (Maastricht NL)
[5]Trilon BD Powder supplied by BASF SE (Ludwigshafen, DE)
[6]POLYOX ™ WSR N-10 (Glyceryl monostearate) supplied by Dow chemicals (Michigan US)
[7]Y-14945 supplied by Momentive Performance Materials The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair care composition comprising:
from about 0.04 wt % to about 2 wt % azelaic acid;
from about 0.04 wt % to about 1 wt % oleic acid;
wherein the ratio of oleic acid to azelaic acid is from about 1:1 to about 1:3 oleic:azelaic;
and an aqueous carrier.

2. The hair care composition of claim 1, wherein the ratio oleic acid to azelaic acid is from about 1:2.5 to about 1:3.

3. The hair care composition of claim 2, wherein the ratio of oleic acid to azelaic acid is from about 1:2 to about 1:3.

4. The hair care composition of claim 3, wherein the ratio of oleic acid to azelaic acid is from about 1:1.5 to about 1:3.

5. The hair care composition of claim 1, wherein the composition comprises from about 0.1 wt % to about 1 wt % azelaic acid.

6. The hair care composition of claim 1, wherein the composition comprises from about 0.1 wt % to about 0.5 wt % oleic acid.

7. The hair care composition of claim 1, further comprising a high melting point fatty compound.

8. The hair care composition of claim 7, wherein the high melting point fatty compound is selected from the group consisting of cetyl alcohol, stearyl alcohol, behenyl alcohol, and mixtures thereof.

9. The hair care composition of claim 8, wherein the composition comprises one or more high melting point fatty compound(s)s at a level of from about 0.1 wt % to about 20 w t%.

10. The hair care composition of claim 9, wherein the composition comprises one or more high melting point fatty compound(s)s from about 1% to about 15%.

11. The hair care composition of claim 1, further comprising a silicone compound.

12. The hair composition of claim 11, wherein the silicone compound is selected from the group consisting of dimethicones, silicone quaternium-26, terminal aminosilicone, and combinations thereof.

13. The hair care composition of claim 1, wherein the hair care composition is a hair conditioner.

14. The hair care composition of claim 13, wherein the hair care composition is a leave on conditioner treatment.

15. The hair care composition of claim 13, wherein the hair care composition is a rinse off conditioner.

16. The hair care composition of claim 1, further comprising a cationic surfactant system.

17. The hair care composition of claim 16, wherein the cationic surfactant system is selected from the group consisting of mono-long alkyl quaternized ammonium salt; a combination of mono-long alkyl quaternized ammonium salt and di-long alkyl quaternized ammonium salt; mono-long alkyl amidoamine salt; a combination of mono-long alkyl amidoamine salt and di-long alkyl quaternized ammonium salt; a combination of mono-long alkyl amidoamine salt and —mono-long alkyl quaternized ammonium salt; and combinations thereof.

18. The hair care composition of claim 17, wherein the composition comprises from about 0.1 wt % to about 10 wt % of the cationic surfactant system.

19. The hair care composition of claim 1, wherein the composition comprises a gel matrix.

20. The hair care composition of claim 19, wherein the gel matrix comprises a cationic surfactant, a high melting point fatty compound, and an aqueous carrier.

* * * * *